United States Patent
Leistner et al.

[11] Patent Number: 5,888,454
[45] Date of Patent: Mar. 30, 1999

[54] DEVICE FOR MEASUREMENT OF LUMINESCENCE OF A FLUID SAMPLE

[75] Inventors: Hermann Leistner, Birkenfeld; Jörg Eppler, Keltern Dietlingen; Martin Trump, Arnbach, all of Germany

[73] Assignee: Stratec Elektronik GmbH, Germany

[21] Appl. No.: 20,987

[22] Filed: Feb. 9, 1998

[30] Foreign Application Priority Data

Feb. 7, 1997 [DE] Germany ............... 197 04 732.4

[51] Int. Cl.⁶ .................................................. G01N 21/76
[52] U.S. Cl. ........................ 422/52; 422/65; 422/104; 436/172; 250/361 C; 356/244; 356/246
[58] Field of Search .................. 422/52, 63, 65, 422/104; 436/172, 805, 809; 356/440, 244, 246; 250/361 C

[56] References Cited

U.S. PATENT DOCUMENTS

| | | | |
|---|---|---|---|
| 5,159,197 | 10/1992 | Wannlund | 250/328 |
| 5,202,091 | 4/1993 | Lisenbee | 422/52 |
| 5,290,513 | 3/1994 | Berthold et al | 422/52 |
| 5,401,465 | 3/1995 | Smethers et al. | 422/52 |
| 5,422,075 | 6/1995 | Saito et al. | 422/52 |
| 5,611,994 | 3/1997 | Bailey et al. | 422/52 |
| 5,682,232 | 10/1997 | Tajima et al. | 356/246 |
| 5,798,263 | 8/1998 | Wood et al. | 435/288.7 |

*Primary Examiner*—Long V. Le
*Attorney, Agent, or Firm*—Pendorf & Cutliff

[57] ABSTRACT

The invention concerns a measuring device for carrying out of luminescence measurements of fluid samples, with a light detector (10) which detects the light entering an aperture opening (36) of a inlet aperture (18) and a positioning device for positioning one of a multiplicity of sample vessels (20) arranged on a micro-test plate (16 with respect to the aperture opening (36). In order to prevent the spill-over of light between the individual sample vessels (20), a transverse shield (42) is provided capable of being brought into engagement with the sample plate, which in the engagement position separates the measurement opening (24) of the sample vessel (20') found in the measurement position from the measurement openings of the adjacent sample vessels (20).

18 Claims, 3 Drawing Sheets

DEVICE FOR MEASUREMENT OF LUMINESCENCE OF A FLUID SAMPLE

BACKGROUND OF THE INVENTION

1. Field of the Invention

The invention concerns a measuring device for carrying out luminescence measurements of fluid samples.

2. Description of the Related Art

Measurement devices of this type are employed primarily in automatic or semi-automatic operated analytic instruments for sequential analytic analysis of chemical and biological systems. The principle of measurement is based upon the detection of a light signal, which is emitted by a reaction partner taking part in a chemiluminescence reaction or by a substance which is stimulated to fluoresce by activation light. Therein even very weak light signals can be measured with high precision with highly sensitive light detectors such as photomultipliers, so that in principle a high detection sensitivity is obtainable.

In known measuring devices of the type described above, an orifice plate is used to interface the inlet cross-section of the photomultiplier to the opening diameter of the sample vessels, which are provided in a matrix-like manner in a micro-test-plate. The orifice plate is provided as a stationary orifice plate, of which the orifices expose the measurement openings of the thereunder situated sample vessels, while the remaining sample vessels are covered over in the upper side with respect to the light detector. It has been found to be disadvantageous therein, that even the smallest gap in the area between the micro-test-plate and the orifice plate suffices to substantially compromise the measurement sensitivity. This is due to the fact that stray light, above all the so-called transference between the individual sample vessels, is diffused via such gaps into the inlet cross-section of the photomultiplier. In addition to this there is the problem that fluorescence of samples in the adjacent vessels may in this manner be triggered prematurely.

SUMMARY OF THE INVENTION

Beginning therewith, the present invention is concerned with the task of increasing the detection sensitivity of the luminescence measurements by suppressing the above-described disruptive effects, in particular the transference of light between adjacent sample vessels.

The invention is based on the concept, that by using "light traps" between the measuring openings of the sample vessels, a direct light transference can be prevented. In order to make this possible, there is proposed according to a first variation of the invention to provide a transverse shield capable of engagement with the sample plate, which in the engagement position surrounds around the sides of a measurement opening of the vessel situated in the measurement position, and separates or shields it from the measurement openings of the adjacent sample vessels. Therewith it is accomplished that in the contact area between the inlet aperture and the sample plate the gaps running between the measurement openings, as can occur for example as a result of manufacturing tolerances of the sample plate, can be blocked at their point of origin, so that a direct light transmission between the sample vessels can substantially be prevented.

Advantageously the transverse barrier is provided with an inner or insert step which engages behind the measurement opening of the sample vessel situated in the measurement position. Therewith the measurement opening is circumferentially surrounded by a rim seam, which particularly effectively impedes any light transference. Here it is particularly advantageous, when the transverse shield extends beginning with the insert step at least to the rim of the measuring opening of the adjacent sample vessel. By this means a further reduction of the light transference is achieved by blocking both the light exiting as well as entry points of the vessels.

Further it is of advantage, when the transverse barrier engages essentially form fittingly in a recess or notch in the upper side of the sample plate. Therewith there is achieved, besides a good shielding, an insuring of maintenance of the engagement position against transverse displacement. Therein it is particularly advantageous when the transverse shielding is formed by a projection on the side opposite the inlet aperture and projecting around the edge of the orifice. In order to facilitate the assuming of the engagement position, the barrier projection can be provided with side flanges arranged diagonally, at acute angles to each other.

During employment of a micro-test plate, which has cylindrical sample vessels arranged matrix-like, with open side end sections along a plane forming a mating surface, the transverse shielding is preferably provided essentially form-complimentary to the interstitial space between the end sections of a sample vessel found in the measurement position and the surrounding sample vessels.

In order that the sample plate can be displaced for positioning of the individual sample vessels without hindrance, the inlet aperture with the transverse shielding is provided moveably between a position raised or elevated above the sample plate and the engagement position. For this the positioning device can be provided with a tilting or pivoting device, by means of which the transverse shielding in fixed connection with the inlet aperture and the light detector is pivotable about a horizontal pivot axis with respect to the sample plate. Thereby it is of advantage when the pivot movement into the engagement position can be carried out by a pull magnet against the force of a return spring. Thereby, even in the case of a defect of the pull magnet, the inlet aperture pivots by itself into position and releases the sample plate.

An alternative embodiment of the invention includes a shield plate which is capable of being engaged on the broad side with the sample plate, which in the engagement position exhibits concentric arranged transverse through holes with respect to the measurement openings of the sample vessels, engaging behind the rims of the measurement openings and separating the measurement openings from the measurement openings of the adjacent sample vessels.

A particularly preferred surrounding of the measurement openings is thereby achieved, when the transverse through holes of the shield plate are formed by orifices, in which the ring-shaped end sections of the cylindrical sample vessels of a sample plate shaped as a micro-test plate engage along a planer connection surface. A further improvement in this respect can thereby be achieved, that the orifices are shaped as step bores of which larger cross-sections form-fittingly engage the end sections of the sample vessels. The shield plate can be provided pivotably as a cover plate upon a sample plate receiving transport frame, wherein the inlet aperture lies upon the surface of one of the upper plan sides of the shield plate.

For carrying out of automatic measurements the positioning device includes a displacement mechanism automatically operated by means of a drive mechanism, upon which the sample plate is securely fixable.

BRIEF DESCRIPTION OF THE DRAWINGS

In the following the invention will be described in greater detail by means of the illustrative embodiments as schematically represented in the figures. There are shown:

FIG. 3b the orifice plate as cover flap of a transport frame containing a micro-test plate in a vertical view along the section lines b—b of FIG. 3a;

DETAILED DESCRIPTION OF THE INVENTION

Figure 1:
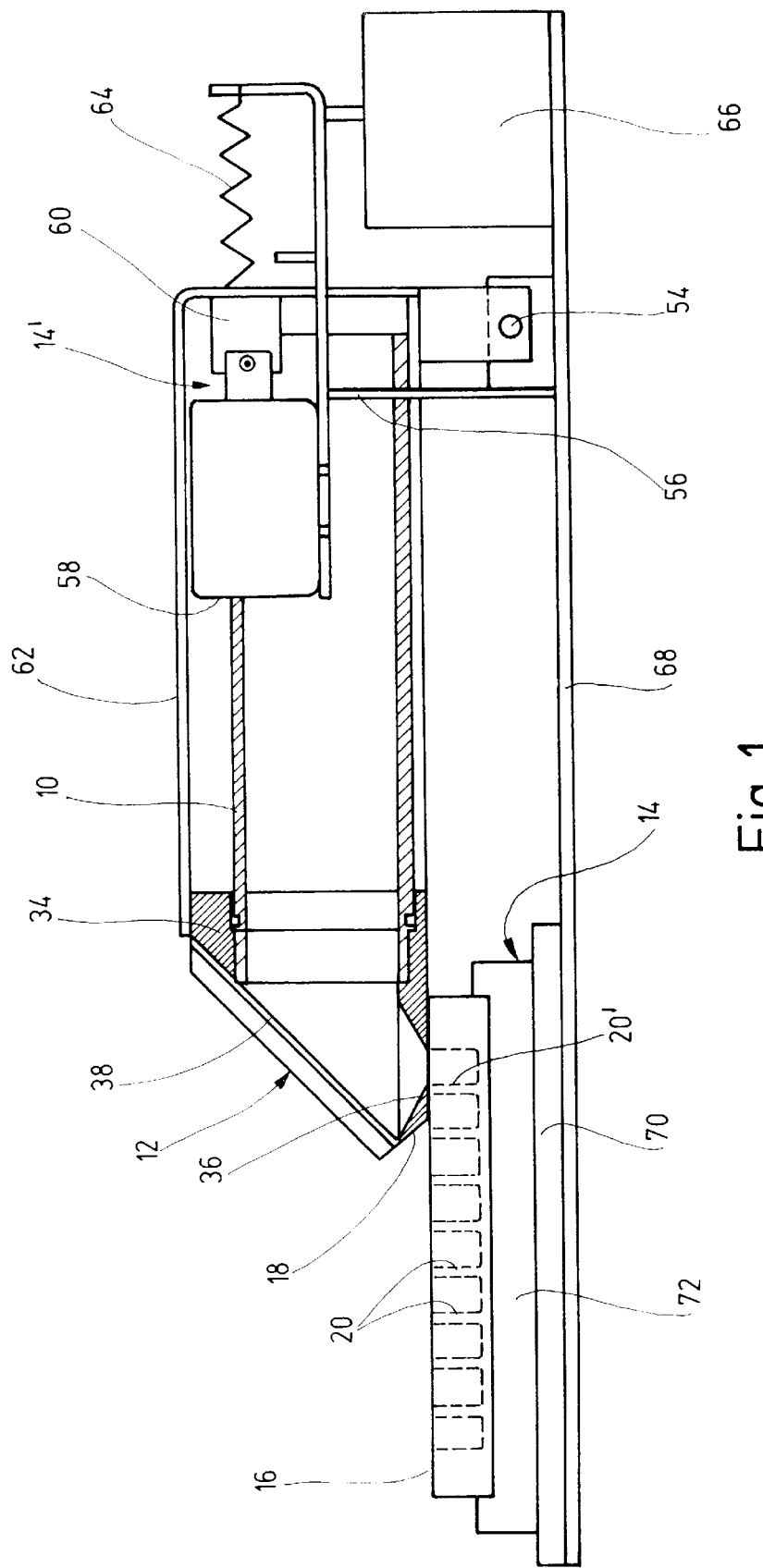
FIG. 1 a measurement device for carrying out of luminescence measurements in a partially sectional side view.

The measuring device shown in the drawings serves for carrying out the chemi-luminescence or fluoresce measurements of liquid samples and is comprised essentially of a horizontally lying oriented photo-multiplier 10 connected to a not shown evaluation electronics, a reflector body 12 provided on the inlet side of the photo-multiplier, and a positioning device 14 for respective positioning of a sample plate 16 and a inlet aperture 18 of the reflector body 12.

Figure 2:
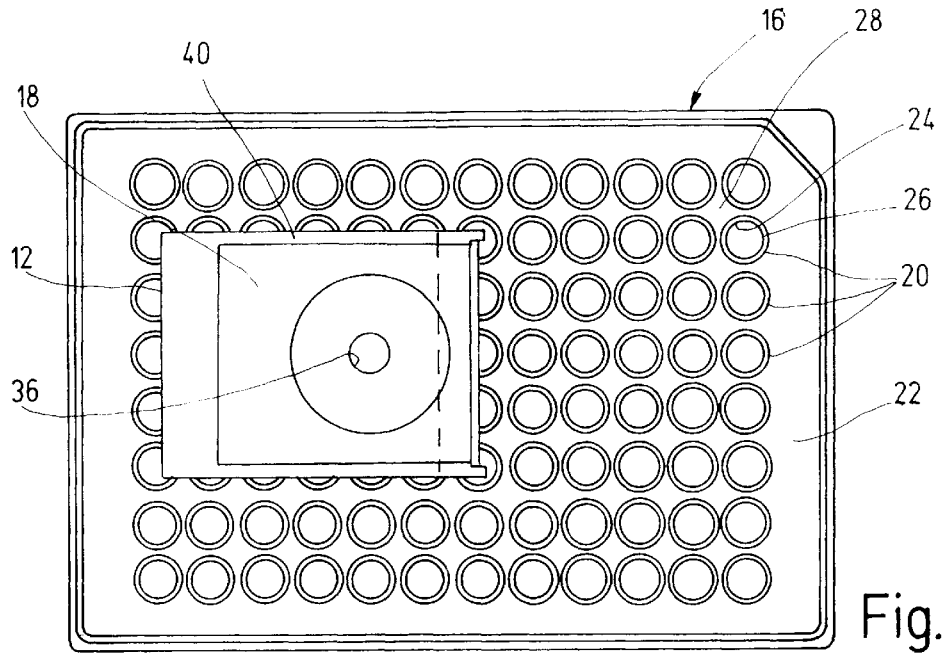
FIG. 2 an inlet aperture of the measurement device according to FIG. 1 in a measurement position over a micro-test plate in the top view.

The measuring device is designed for receiving a standardized sample plate 16, which, as a so-called micro-test-plate is constituted as a single piece of plastic and includes in the shown embodiment 8×12 cylindrical sample vessels 20 arranged matrix-like (FIG. 2). The sample vessels 12 go through a common or connecting wall 22 on the upper broad side of the sample plate 16 and project above this with their measurement opening 24 defining ring-shaped end sections 26. The measurement openings 24 are therewith bordered at their rims by an interstitial area or, as the case may be, recess area 28, which is limited vertically by the outer contour of the end sections 26 and via the connecting wall 22 on the floor side. Below the connection wall 22 the sample vessels 20 are connected with each other at their radial steps 30.

The reflector body 12 is seatable upon a step bore 32 of a section 34 of the photo-multiplier 10 and is fixedly connectable therewith. In the lower area of this section 34 the inlet aperture 18 is perpendicular opposite to the inlet opening of the photo-multiplier and is broken through by a conically upwardly broadening aperture opening 36. A plan mirror 38 is provided between side walls 40 which on the sides close off the reflector body 12 in a light tight manner and which redirects the measurement light entering through the aperture opening into the photo-multiplier 10. Thereby, in the measuring position, the inlet cross-section of the aperture opening 36 is positioned or oriented concentrically to the measurement opening 24 of the sample vessel 20.

In order to prevent the penetration of stray light and also to prevent an exchange of gas-like reaction materials, a transverse covering is provided, which at least in the sample vessel 20' found in the measurement position engages around a recess area 28 on the upper side of the sample plate 16.

Figure 4:
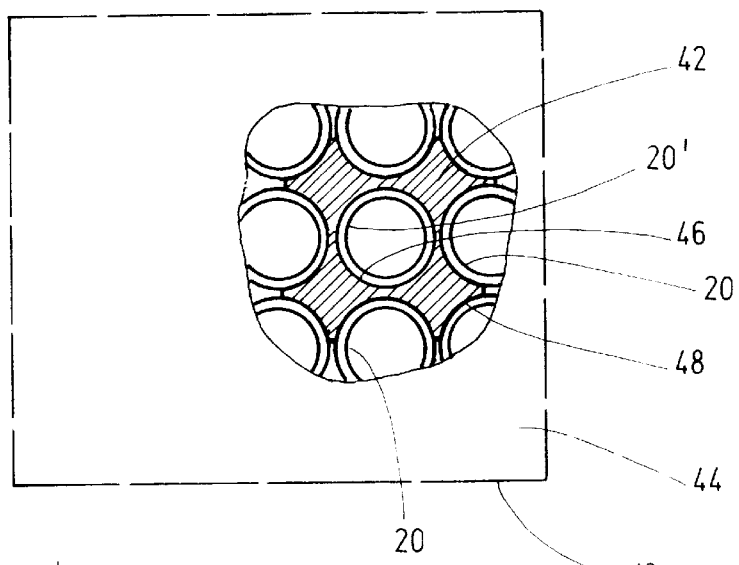
FIG. 4 a transverse shielding in the engagement position on the seating or supported side, opposite to the inlet aperture as shown in FIG. 2, in a partial horizontal section at the elevation of the seating side.
Figure 5:
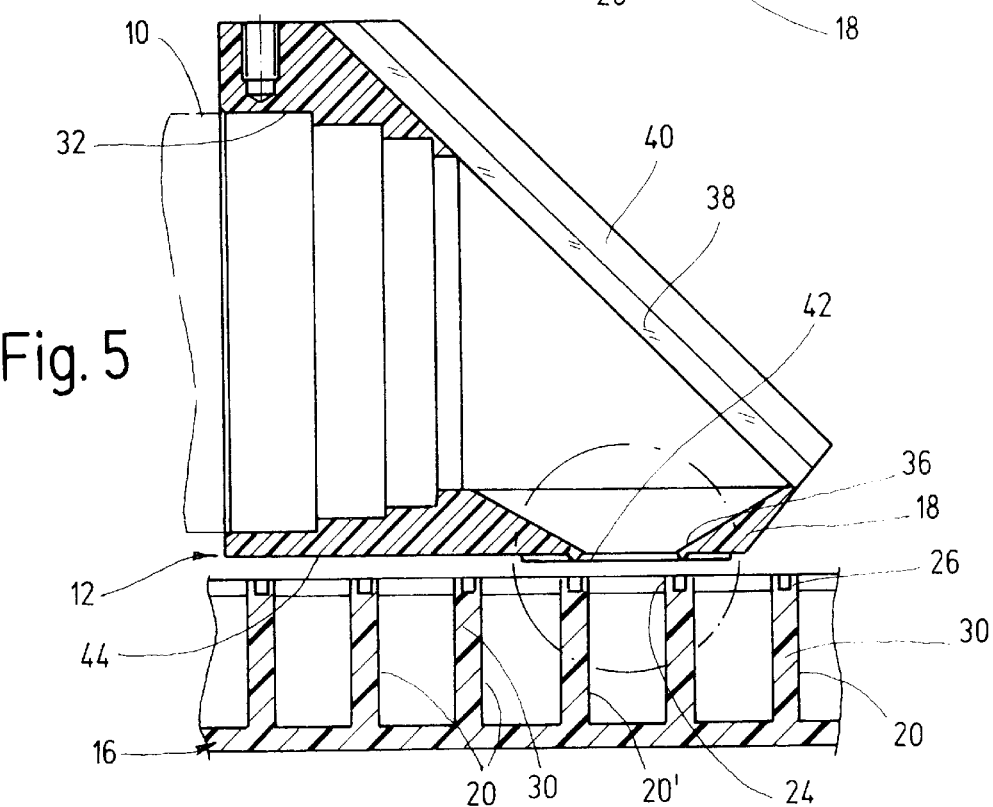
FIG. 5 a vertical sections through a inlet aperture according to FIG. 2 and 4 comprising reflector body in a position lifted above the micro-test plate.
Figure 6:
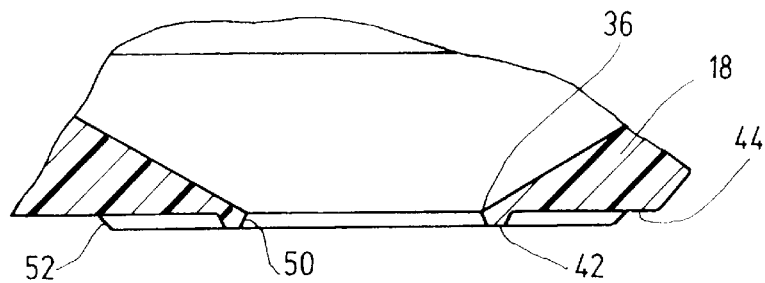
FIG. 6 a sectional enlargement according to FIG. 5.

In the embodiment shown in the FIGS. 2 and 4 through 6 the transverse covering is formed by a shield projection 42, of which a sample plate 16 facing mating surface 44 projects downwards beyond the inlet aperture 18 and surrounds the aperture opening 36 about the rim. The shield projection 42 is provided with a ring-shaped inner step 46 and a Maltese Cross-shaped outer step 48 formed complimentary to the upper surface contour of the sample plate 16 (FIG. 4). Therewith an engagement registry can be produced, in which the shutter continuation 42 form fittingly engages in the recess area 28 between the sample vessels 20. The engagement is thereby facilitated, that the outer and inner step 46, 48 are provided with side flanks 50, 52 arranged at acute or inclined angles diagonally to each other (FIG. 6).

In order to release the sample plate 16 for positioning, a tilt device or apparatus 14' is provided by means of which the reflector body 12 together with the photo-multiplier 10 is pivotable about a horizontal pivot axis 54, so that the shutter continuation 42 is lifted out of the engagement position into a station lifted above the sample plate as shown in FIG. 5. The pivot device 14' is comprised a pull magnet 58 mounted fixedly upon an assembly wedge 56, of which the anchor engages the pull cover plate 60 of a housing 62 which receives the photo-mulitplier 10, upon the tilt axis 54 mounted housing 62. A pull spring 64 engaging on the housing 62 insures assuming of a position defined by an abutment when the pull magnet 58 is not operating.

An X-Y displacement mechanism 14 serves for positioning of the individual sample vessels 20 in the measuring position, upon which the sample plate 16 can be fixed, and which by means of a drive unit 66 is automatically operable. The displacement mechanism 14 is comprised of two displacement sleds 70, 72 coupled to each other and displaceable along guide paths arranged at right angles to each other over a fixed floor plate 68. The above described embodiment is intended above all for employment in fully automatic functioning measuring devices, in which sample plates filled by a titration device are automatically driven in and out of the measuring device.

Figure 3A:
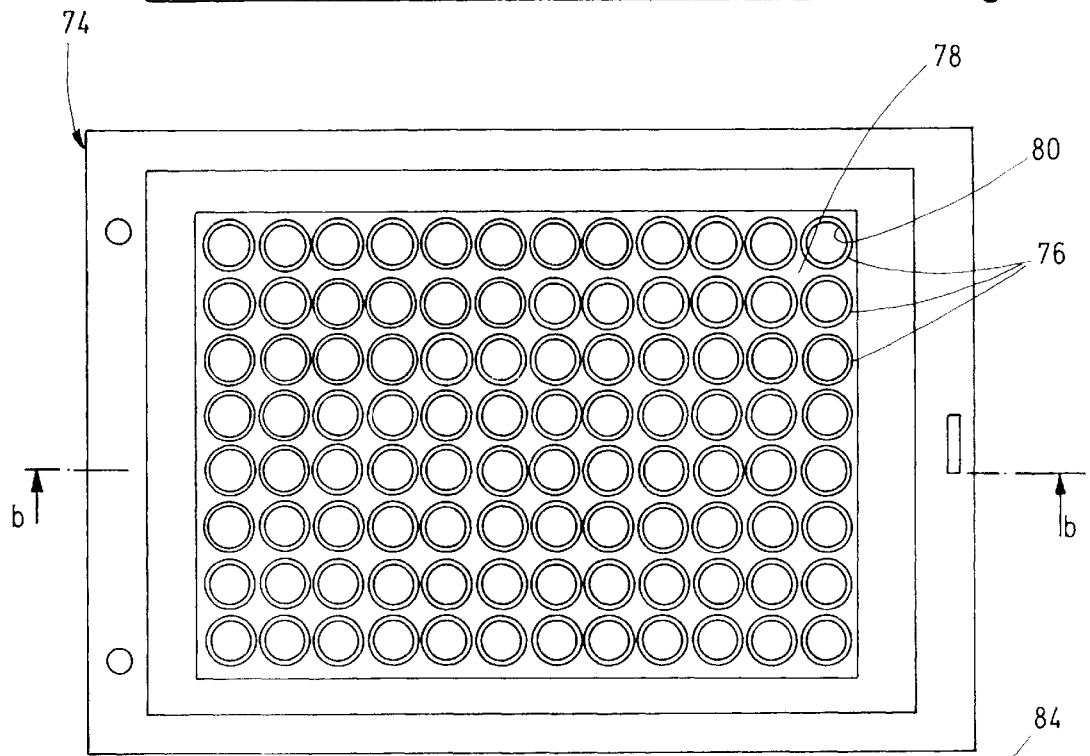
FIG. 3a a shield orifice plate in a broad side view from below.

In the embodiment shown in FIG. 3, the transverse shielding is formed by a shield plate 74, of which the broad side is capable of being brought into engagement with sample plate 16. The shield plate 74 exhibits for this a number of step apertures 76 corresponding to the sample vessels 20 of the sample plate 16, of which the lower, the larger diameter exhibiting side, form-sealingly engages the end sections 26 of the sample vessels 20. In the engagement position the recessed area 28 of the sample plate 16 is essentially completely filled up by the form complimentary, the step bore hole 76 bordering contact or sealing area 78, so that the measurement openings 24 of the sample vessels 20 are shielded sideways from each other. Towards upwards the measurement openings 24 align with smaller diameter sections of the step bore holes 76, so that the measurement light can be radiated upwardly outwards without impediment.

Figure 3B:
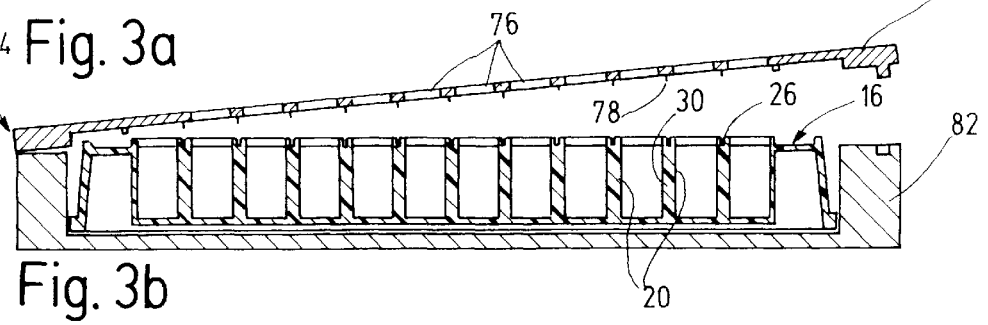

As shown in FIG. 3b, the shield plate 74 is pivotably or hingedly provided on a transport frame 82 securable to sliding or floating sled 72 which is designed to receive the sample plate 16. In the measurement process the inlet aperture 18 lies with its seating side 44 flat or flush on the planar surface 84 of the shield plate 74. The inlet aperture 18 exhibits in this embodiment no shield projection and is not lifted during the displacement of the sample plate 16 in the individual measurement positions, but rather glides on the shield plate 74. This embodiment is particularly suitable above all for a semi-automatic functioning device, in which the sample plate must be manually introduced into the transport frame.

In summary the following is to be concluded. The invention concerns a measuring device for carrying out of luminescence measurements of fluid samples, with a light detector 10 which detects the light entering an aperture opening 36 of a inlet aperture 18 and a positioning device for positioning one of a multiplicity of sample vessels 20 arranged on a micro-test plate 16 with respect to the aperture opening 36. In order to prevent the spill-over of light between the individual sample vessels 20, a transverse shield 42 is provided capable of being brought into engagement with the sample plate, which in the engagement position separates the measurement opening 24 of the sample vessel 20' found in the measurement position from the measurement openings of the adjacent sample vessels 20.

What is claimed is:

1. Measurement device for effecting luminescence measurements of fluid samples, comprising:
    a sample plate including a plurality of sample vessels (20) having upper measurement openings (24) through which measurement light passes, said measurement openings having outer rim edges,
    a positioning device (14, 14') for positioning one of said sample vessels (20) in a measurement position,
    a transverse shield (42) including an inlet aperture (18) having an aperture opening (36), said transverse shield provided between said sample vessel (20) and a light detector (10),
    a light detector (10) for detecting the light passing through the aperture opening (36) of an inlet aperture (18) of said transverse shield (42),
    wherein when said transverse shield (42) is brought into engagement with the sample plate (16), it engages behind the outer rim edges of the measurement opening (24) of the sample vessel (20') found in the measurement position and separates it from the measurement openings (24) of the adjacent sample vessels (20).

2. Measurement device according to claim 1, wherein said light detector (10) is a photo-multiplier.

3. Measurement device according to claim 1, wherein said transverse shield (42) is provided with an inner step (46) which engages around the outer rim edges of the measurement opening (24) of the sample vessel (20') situated in the measurement position.

4. Measurement device according to claim 1, wherein the transverse shield (42) extends from the measurement opening (24) of the sample vessel (20') situated in the measurement position at least to the bordering rim edges of the measurement opening (24) of the adjacent sample vessel (20).

5. Measurement device according to claim 1, wherein the transverse shield (42) form fittingly engages in a recess (28) on an upper side of the sample plate (16).

6. Measurement device according to claim 1, wherein the transverse shield includes, on the side of a seating surface (44) facing the sample plate (16), a barrier projection (42) which projects beyond the inlet aperture (18) and surrounds the aperture opening (36).

7. Measurement device according to claim 6, wherein the shield projection (42) exhibits side flanks (50, 52) which are slanted at acute angles to each other.

8. Measurement device according to claim 1, wherein said sample plate is constructed as a micro-test-plate (16), on which in a matrix-form orientation cylindrical sample vessels (20) project with open side end sections (26) above a horizontal or planar connection surface (22) as sample vessels, and wherein the transverse shield (42) is formed essentially form-fitting to a recess defined by an interstitial area (28) between end sections (26) of one of the sample vessels (20') situated in the measurement position and the surrounding sample vessels (20).

9. Measurement device according to claim 1, wherein the transverse shield (42) carrying inlet aperture (18) is provided moveably between a position raised from the sample plate (16) and an engagement position.

10. Measurement device according to claim 1, wherein the positioning device (14, 14') includes a pivot device (14'), by means of which the transverse shield (42) in rigid connection with the inlet aperture (18), and optionally the light detector (10), is pivotable about a horizontal pivot axis (54) with respect to the sample plate (16).

11. Measurement device according to claim 10, wherein the pivot movement into the engagement position is carried out by means of a pull magnet (58) against the force of a return spring (64).

12. Measurement device according to claim 1, wherein the positioning device (14, 14') is comprised of an automatically operated displacement mechanism (14) operated by means of a drive unit (66), on which the sample plate (16) is mounted.

13. Measurement device for effecting luminescence measurements of fluid samples, comprising:
    a sample plate including a plurality of sample vessels (20) having upper measurement openings (24) through which measurement light passes, said measurement openings having outer rim edges,
    a positioning device (14, 14') for positioning one of said sample vessels (20) in a measurement position,
    a transverse shield plate (74) having one side capable of being brought into engagement with said measurement openings of said sample plate (16), said transverse shield plate provided between said sample vessel (20) and a light detector (10),
    a light detector (10) for detecting the light passing through an aperture opening (36) of an inlet aperture (18) of said transverse shield (42),
    wherein said transverse shield plate (74) exhibits a number of apertures (76) corresponding to the sample vessels (20) of the sample plate (16), which apertures engage around and behind the outer rim edges of the measurement opening (24) of the sample vessel (20') found in the measurement position and separate it from the measurement openings (24) of the adjacent sample vessels (20).

14. Measurement device according to claim 13, wherein the sample plate is formed as a micro-test-plate (16) with ring-shaped end segments (26) of a cylindrical sample chamber encompassing sample vessels (20) following a horizontal surface (22), into which end segments the apertures of the shield plate (74) formed as concentric step apertures (76) engage.

15. Measurement device according to claim 14, wherein the apertures are formed as step bore holes (76), in a cross-section of which are adapted to form-fittingly engage the end segments (26) of the sample vessels (20).

16. Measurement device according to claim 13, wherein the shield plate (74) is pivotably provided as a cover plate on one of transport frames (82) for receiving the sample plate (16).

17. Measurement device according to claim 13, wherein the inlet aperture (18) lies flat upon an upper plan side (84) of the shield plate (74).

18. Measurement device according to claim 13, wherein the positioning device (14, 14') is comprised of an automatically operated displacement mechanism (14) operated by means of a drive unit (66), on which the sample plate (16) is mounted.

* * * * *